United States Patent [19]

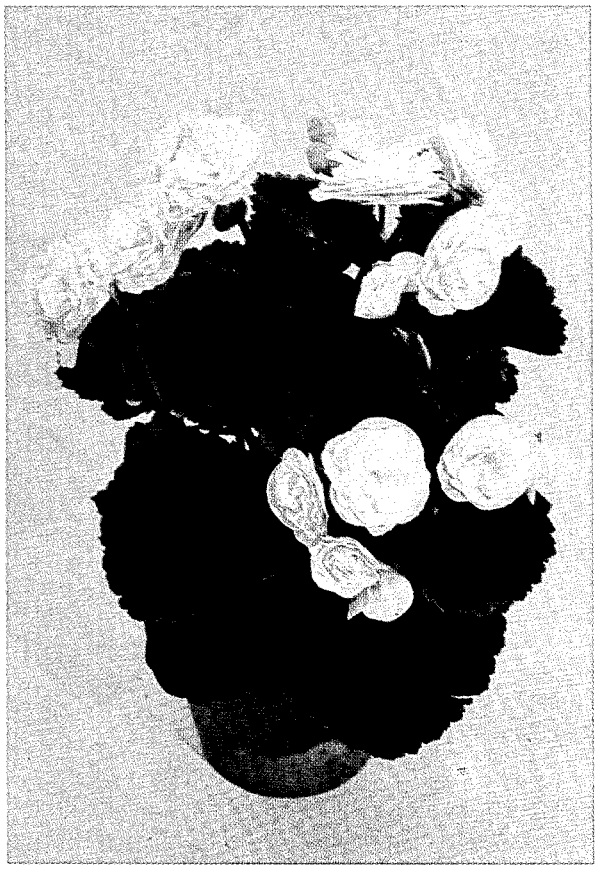

Rohde

[11] Plant 4,124

[45] Oct. 11, 1977

[54] BEGONIA PLANT

[75] Inventor: Hans-Joachim Rohde, Nurtingen, Germany

[73] Assignee: Mikkelsens Inc., Ashtabula, Ohio

[21] Appl. No.: 715,101

[22] Filed: Aug. 17, 1976

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

This novel begonia originated as a mutation of Ballerina, and has bright yellow tepals.

1 Drawing Figure

1

The present invention relates to a new and distinctive cultivar of begonia plant, botanically known as *Begonia elatior,* and was discovered by me as a mutation of the cultivar Ballerina, disclosed in U.S. Plant Pat. No. 3,868, issued Apr. 20, 1976 to Margarete Rohde-Rieger. The new cultivar was observed in a group of flowering plants of the parent cultivar Ballerina. Asexual reproduction by stem and leaf cuttings has reproduced the unique features of the cultivar through successive propagations.

The following characteristics in combination distinguish the new begonia from both its parent and other begonias commercially known and used in the floriculture industry:

1. Bright yellow double flower up to 6 cm. in diameter when mature. The parent cultivar Ballerina is apricot-orange in color.
2. Flowers are double with odd numbers of tepals, varying in number more or less from 21 to 31.
3. The new cultivar is very fast growing and requires growth regulators for height control when produced under a high light and temperature environment.
4. General plant characteristics somewhat resemble the Rieger Aphrodite types, but better stem vigor allows this new cultivar to be better adapted to upright growth. Reference is made to U.S. Plant Pat. No. 3,318 (Aphrodite Cherry Red).
5. The new cultivar is highly resistant to common, powdery mildew.
6. Individual flowers are long lasting but of less duration than the parent cultivar Ballerina.

The accompanying colored photographic drawing taken in Nurtingen, Germany illustrates the overall appearance of the new cultivar taken as a face view of the plant. The photograph shows the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

Parentage: The new cultivar is a mutation of the cultivar Ballerina.

Propagation: Propagation is very rapid by leaf cuttings, being 2 weeks faster than Schwabenland, disclosed in U.S. Plant Pat. No. 3,320, granted Mar. 13, 1973 to

2

Otto Rieger, deceased. Initiation and development of 3-6 adventitious buds is very consistant at all times of the year and especially good in summer months when the Schwabenland types are inconsistent. Stem cuttings may also be used for propagation as there is considerable self-branching.

*Rooting habits.*—Very easy to root at 20°-22° C. Roots are abundant, fibrous, and have a dendritic pattern.

*Plant form.*—Basically upright, tending to be vining under high light environments.

*Habit of Growth.*—Very free growing.

*Blooming habits.*—After flower initiation, there is profuse blooming over a long period of time.

*Blooming season.*—Natural flowering season is in November in Germany. By use of controlled environments of temperature and daylight Balaleika can be commercially produced at all times of the year.

*Foliage.*—Near average for this type of begonia.

*Size.*—15 cm. across by 12 cm. long. Leaf size will vary with growing conditions.

*Shape.*—Nearly round.

*Texture.*—Leathery.

*Margin.*—Nearly complete with few serrations or sinus indentations. Young leaves are sharply serrated.

*Color.*—Young leaves: Upper side, darker than 147A green. Lower side, green mixed with red. Mature leaves: Upper side, darker than 139A green. Lower side, 147C yellow green.

*Disease resistance.*—More resistant to powdery mildew than the Schwabenland types but somewhat less resistant than the Aphrodite types when all are tested under conditions for optimum mildrew growth.

Flowers:

*Borne.*—On strong upright peduncles. Flowers are double with average of 25 tepals. Odd numbers of tepals usually occur. Edges of flowers are sometimes very wavy.

*Quantity.*—Average for elatior type begonias. Long lasting double flowers and variable color tones give an appearance of greater flowering.

*Buds.*—Flat, measuring 25 mm. in diameter before flowering.

*Tepals.*—Total flower size 45 mm. to 60 mm. in diameter.

*Color.*—The flower color is yellow 9A fading to 9C. The outer two petals may show slight red infusion on the underside of the tepals.

Reproductive organs:

*Stamens.*—None seen to date.

*Pollen.*—None seen to date.

*Styles/ovaries.*—None seen to date.

I claim:

1. A new and distinct cultivar of begonia plant characterized particularly as to uniqueness by the combined characteristics of bright yellow double flowers having a size up to 6 cm. in diameter when mature, with the flowers having an odd number of tepals; very fast growing habit which requires growth regulation for height control in high light and high temperature conditions, and long lasting nature of the individual flowers.

* * * * *

UNITED STATES PATENT OFFICE
CERTIFICATE OF CORRECTION

PATENT NO. : PP-4124

DATED : October 11, 1977

INVENTOR(S) : HANS-JOACHIM ROHDE

It is certified that error appears in the above-identified patent and that said Letters Patent are hereby corrected as shown below:

Column 1, line 3, after "elatior" insert --(hiemalis-Fotsch)--.

Column 1, line 34, delete "taken in Nurtingen, Germany--.

Column 2, line 43, delete "variable color tones".

Signed and Sealed this

*Twenty-eighth* Day of *March 1978*

[SEAL]

*Attest:*

RUTH C. MASON
*Attesting Officer*

LUTRELLE F. PARKER
*Acting Commissioner of Patents and Trademarks*